March 19, 1974 W. H. JESSEL, JR., ET AL Plant Pat. 3,521
CHRYSANTHEMUM PLANT
Filed Aug. 10, 1971
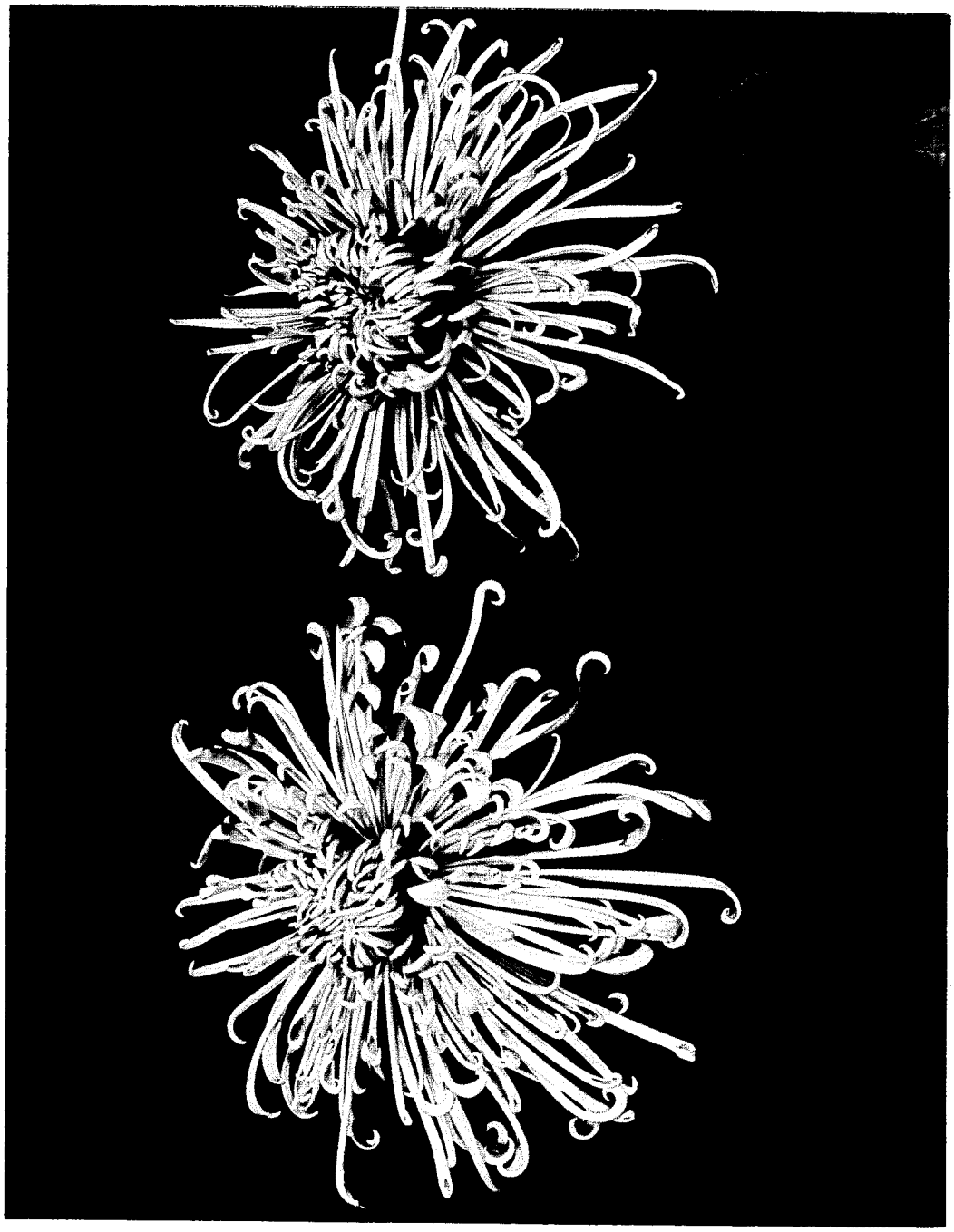

United States Patent Office

Plant Pat. 3,521
Patented Mar. 19, 1974

3,521
CHRYSANTHEMUM PLANT

Walter H. Jessel, Jr., Doylestown, and William E. Duffett, Akron, Ohio, assignors to Yoder Brothers, Inc., Barberton, Ohio

Filed Aug. 10, 1971, Ser. No. 170,669
Int. Cl. A01h *5/00*
U.S. Cl. Plt.—79 1 Claim

The present invention comprises a new and distinct cultivar of chrysanthemum plant which is a sport of the unpatented cultivar known in the United States as Streamer.

The new cultivar is similar in many respects to Streamer, having the same characteristics of:

(1) A spider flower form.
(2) Foliage shape.

The new cultivar is distinguished from Streamer by the following characteristics when grown under comparable conditions:

(1) Its bronze color.
(2) Approximately 3" more vigor.
(3) Two to three days later response.
(4) Foliage ¼" to ½" shorter in length.
(5) The petals are straighter tubes, with a narrower diameter and less in curving of the petal tips.
(6) A flower approximately ½" larger diameter.
(7) A greater seasonal variation in flower form and petal count than the parent. In late fall (approximately November through mid-December) and late spring (approximately mid-March through April), the form is more incurved and the petal count is similar to that of Streamer. In low light periods (approximately late December through early March) Bronze Streamer has a reduced petal count and less incurvature of the petals than in higher light periods. These seasonal variations are less pronounced in Streamer.

The new cultivar was selected from a flowering block of the parent cultivar at Barbarton, Ohio, and when asexually reproduced by cuttings at Barberton, Ohio has been found to retain its distinctive characteristics through successive propagations.

Our new cultivar when grown in the vicinity of Barberton, Ohio, has a response period of approximately 10 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from November through mid-May; coastal California, October through May; and Florida, December through March.

In the accompanying drawing, the new cultivar appears on the left and the parent cultivar streamer on the right.

In the description which follows, color references are made to the Munsell Color Book, 1963 edition, and comparisons are made with the parent cultivar Streamer. Where a single value or description appears for the new cultivar only, the same value or description applies to the parent cultivar.

Botanical classification: *Chrysanthemum morifolium*

| | Bronze Streamer | Streamer |
|---|---|---|
| Bloom: | | |
| Size | Approximately 7" | Approximately 6½". |
| Fully expanded | Approximately 7½" | Approximately 7". |
| Borne | Singly on disbudded plants | |
| Stems | Strong | |
| Form | Tubular flaring to spoon at tip, tapering to a hooded point, less incurved at petal tips. | Tubular flaring to spoon at tip, tapering to a hooded point. |
| Permanence | 12–14 days | |
| Color | | |
| Center of flower | Yellow bronze, 7.5R7/4 | Lavender, 7.5P8/4. |
| Base of petals | Yellow, 7.5Y8.50/6 | Pale lavender, 5RP9/1. |
| Inside of petals | Brick red, 2.5R4/8 to yellow, 7.5Y8.50/6 | Dark lavender, 3.75RP5/12 to lavender 7.5P8/4. |
| Reverse of petals | Light bronze, 7.5R6/4 to yellow bronze, 7.5R7/4 | Light lavender, 10P7/6. |
| Tonality from a distance | Bronze | Lavender. |
| Discoloration | Buff, 5YR8/2 | Lavender, 5RP8/2. |
| Petals: | | |
| Texture | Smooth | |
| Appearance & form | Tubular, flaring to a spooned tip with a hooded, curled curled point. | A thicker tube, flaring to a spooned tip with hooded, curled point. |
| Arrangement | Composite, whorled on a single receptacle | |
| Persistence | Resists shatter | |
| Fragrance | Typical chrysanthemum | |
| Reproductive organs: | | |
| Stamen, anthers | None | |
| Pollen | do | |
| Arrangement | Clustered in center of flower, if present | |
| Styles | Present in both ray & dics florets | |
| Length | Short | |
| Ovaries | At the base of petal attached to receptacle | |
| Plant: | | |
| Form | Herbaceous | |
| Growth | Upright | |
| Height | Approximately 40" when given 3 to 5 long day weeks and a total crop time of 13 to 15 weeks as defined in the timetables of Yoder Brothers, Inc. for the various seasons of the year. | Approximately 37" when given 3 to 5 long day weeks and a total crop time of 13 to 15 weeks as defined in the timetables of Yoder Brothers Inc. for the various seasons of the year. |
| Spread | None | |
| Foliage: | | |
| Top side | Dark green, 7.5GY3/4 | Dark green, 7.5GY3/4. |
| Size | 6½" long, 3¼" wide | 7" long, 3¾" wide. |
| Quantity | Numerous | |
| Shape | Spatulate lobed | |
| Texture | Smooth | |
| Ribs & veins | Prominent | |
| Edge | Deeply indented | |
| Serration | Very slight | |
| Under side | Light green, 7.5GY5/4 | |
| Stipules | Prominent | |

We claim:

1. A new and distinct cultivar of chrysanthemum characterized particularly as to its uniqueness when compared to the parent cultivar Streamer by its bronze color, approximately 3″ more vigor when grown under comparable conditions, two to three days later response, foliage ¼″ to ½″ shorter in length, its petals which comprise straighter tubes with a narrower diameter and less incurving of the petal tips, by its flowers which are approximately ½″ larger in diameter, and by its greater seasonal variation in flower form and petal count than the parent.

No references cited.

ROBERT E. BAGWILL, Primary Examiner